(12) United States Patent
Wallach et al.

(10) Patent No.: US 7,083,788 B2
(45) Date of Patent: Aug. 1, 2006

(54) MODULATORS OF THE FUNCTION OF RECEPTORS OF THE TNF/NGF RECEPTOR FAMILY AND OTHER PROTEINS

(75) Inventors: David Wallach, Rehovot (IL); Andrei Kovalenko, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/927,458

(22) Filed: Aug. 13, 2001

(65) Prior Publication Data

US 2002/0058024 A1     May 16, 2002

Related U.S. Application Data

(63) Continuation-in-part of application No. 09/381,358, filed as application No. PCT/IL98/00125 on Mar. 19, 1998, now abandoned.

(30) Foreign Application Priority Data

Mar. 19, 1997  (IL) .................................... 120485

(51) Int. Cl.
  *A61K 38/17*  (2006.01)
  *C07K 14/435* (2006.01)
(52) U.S. Cl. ..................... 424/185.1; 530/350
(58) Field of Classification Search .............. 530/350; 424/185.1
See application file for complete search history.

(56) References Cited

U.S. PATENT DOCUMENTS 5,871,726 A    2/1999  Henderson et al.
6,232,081 B1 *  5/2001  Harper et al.

FOREIGN PATENT DOCUMENTS

WO    96 25941    8/1996

OTHER PUBLICATIONS

Lin et al, Molecular and Cellular Biology 18(10): 5899-5907, Oct. 1998.*
Kim et al, Oncogene 19(39): 4491-9, Sep. 2000.*
Skolnick et al, From genes to protein structure and function: novel applications of computational approaches in the genomic era, Jan. 2000, TIBTECH 18: 34-39.*
Whisstock et al, Quarterly Reviews of Biophysics 36: 307-340, 2003.*
Ito et al, Proc Natl Acad Sci 98(8): 4569-4574, Apr. 2001.*
Stanger et al., "RIP: A Novel Protein Containing a Death Domain That Interacts with Fas/APO-1 (CD95) in Yeast and Causes Cell Death", *Cell*, vol. 81, pp. 513-523, (1995).
Chinnaiyan et al., "FADD, a Novel Death Domain-Containing Protein, Interacts with the Death Domain of Fas and Initiated Apoptosis", *Cell*, vol. 81, pp. 505-512, (1995).
Hsu et al., "The TNF Receptor 1-Associated Protein TRADD Signals Cell Death and NF-κB Activation", *Cell*, vol. 81, pp. 495-504, (1995).
Malinin et al., "MAP3K-related kinase involved in NF-κB induction by TNF, CD95 and N-1", *Nature*, vol. 385, pp. 540-544, (1997).
Duan et al., "RAIDD is a new 'death' adaptor molecule", *NATURE*, vol. 385, pp. 86-89, (1997).
Ahmad et al., "CRADD, a Novel Human Apoptotic Adaptor Molecule for Caspase-2, and FasL/Tumor Necrosis Factor Receptor-interacting Protein RIP", *Cancer Research*, vol. 57, pp. 615-619, (1997).
Verma et al., *Nature*, 389:239-242, especially p. 239.
Anderson et al., *Nature*, 392:25-30, especially pp. 25 and 30.
Adams et al., *Nature*, 377(6547 Suppl):3-174, See enclosed sequence alignment.
Itoh et al., *Cell*, 233-243, See abstract; p. 236, column 1, first full paragraph, lines 3-15, and Fi. 3; p. 241, column 1, second full paragraph, lines 8-12.
Ngo et al., *The Protein Folding Problem and Tertiary Structure Prediction*, Merz et al(ed.), Birkhauser, Boston, MA pp. 492-495 (1994).

* cited by examiner

*Primary Examiner*—Christina Chan
*Assistant Examiner*—Phuong N Huynh
(74) *Attorney, Agent, or Firm*—Browdy and Neimark, PLLC

(57) ABSTRACT

Proteins which are capable of modulating/mediating the function of RIP, their preparation and uses are provided.

8 Claims, 2 Drawing Sheets

```
tagggagacc caagcttctc gacggccatt accaatcgcg aaaccggcag ggcggccact    60
gtggcggggc tctttccccg tttcgcctca gctacccctc agctccggta gtcgccagtc   120
cggggtcgtc gccgtttggg gcgggagctg ctcggcsccg ccgccgtccc cgtcgccgct   180
tccgggtcca ggccctcgg gccgcctgcc gccgtcatga ggctgcgggt gcggcttctg    240
aagcggacct ggccgctgga ggtgcccgag acggagccga cgctggggca tttgcgctcg   300
cacctgaggc tgtccctgct gtgcacctgg gggtacagtt ctaatacccg atttacaatt   360
acattgaact acaaggatcc cctcactgga gatgaagaca ccttggcttc atatgggatt   420
gtttctgggg acttgatatg tttgattctt caagatgaca ttccagcgcc taatatacct   480
tcatccacag attcagagca ttcttcactc cagaataatg agcaaccctc tttggccacc   540
agctccaatc agactagcat gcaggatgaa caaccaagtg attcattcca aggacaggca   600
gcccagtctg gtgtttggaa tgacacagt atgttagggc ctagtcaaaa ttttgaacct    660
gagtcaattc aagataatgc gcatatggca gagggcacag gtttctatcc ctcagaaccc   720
atgctctgta gtgaatcggt ggaagggcaa gtgccacatt cattagagac cttgtatcaa   780
tcagctgact gttctgatgc caatgatgcc ttgatagtgt tgatacatct tctcatgttg   840
gagtcaggtt acatacctca gggcaccgaa gccaagcac tgtccatgcc gcagaagtgg    900
aagttgagcg gggtgtataa gctgcagtac atgcatcctc tctgcgaggg cagctccgct   960
actctcacct gtgtgccttt gggaaacctg attgttgtaa atgctacact aaaaatcaac  1020
aatgagatta gaagtgtgaa aagattgcag ctgctaccag aatcttttat ttgcaaagag  1080
aaactagggg aaaatgtagc caacatatac aaagatcttc agaaactctc tcgcctcttt  1140
aaagaccagc tggtgtatcc tcttctggct tttacccgac aagcactgaa cctaccagat  1200
gtatttgggt tggtcgtcct cccattgcaa ctgaaactac ggatcttccg acttctggat  1260
gttcgttccg tcttgtcttt gtcgcggtt tgtcgtgacc tcttactgc ttcaaatgac    1320
ccactcctgt ggaggttttt atatctgcgt gattttcgag acaatactgt cagagttcaa  1380
gacacagatt ggaaagaact gtacaggaag aggcacatac aaagaaaaga tccccgaaa   1440
gggcggtttg tgatgctcct gccatcgtca actcacacca ttccattcta tcccaacccc  1500
ttgcacccta ggccatttcc tagctcccgc cttcctccag gaattatcgg gggtgaatat  1560
gaccaaagac caacacttcc ctatgttgga gacccaatca gttcactcat tcctggtcct  1620
ggggagacgc ccagccagtt tcctccactg agaccacgct tgatccagt tggcccactt   1680
ccaggaccta accccatctt gccagggcga ggcggcccca atgacagatt tcccttaga   1740
cccagcaggg gtcggccaac tgatggccgg ctgtcattca tgtgattgat ttgtaatttc  1800
atttctggag ctccatttgt ttttgtttct aaactacaga tgtcaactcc ttggggtgct  1860
gatctcgagt gttattttct gattgtggtg ttgagagttg cactcccaga aacctttaa   1920
gagatacatt tatagcccta ggggtggtat gacccaaagg ttcctctgtg acaaggttgg  1980
ccttgggaat agttggctgc caatctccct gctcttggtt ctcctctaga ttgaagtttg  2040
ttttctgatg ctgttcttac cagattaaaa aaaagtgtaa attaaaaaaa aaaaaaaaa   2100
aaaaaaaaaa aaaaaaaa                                                2119
```

FIGURE 1

```
MRLRVRLLKR  TWPLEVPETE  PTLGHLRSHL  RQSLLCTWGY  SSNTRFTITL  NYKDPLTGDE   60
ETLASYGIVS  GDLICLILQD  DIPAPNIPSS  TDSEHSSLQN  NEQPSLATSS  NQTSMQDEQP  120
SDSFQGQAAQ  SGVWNDDSML  GPSQNFEAES  IQDNAHMAEG  TGFYPSEPML  CSESVEGQVP  180
HSLETLYQSA  DCSDANDALI  VLIHLLMLES  GYIPQGTEAK  ALSMPEKWKL  SGVYKLQYMH  240
PLCEGSSATL  TCVPLGNLIV  VNATLKINNE  IRSVKRLQLL  PESFICKEKL  GENVANIYKD  300
LQKLSRLFKD  QLVYPLLAFT  RQALNLPDVF  GLVVLPLELK  LRIFRLLDVR  SVLSLSAVCR  360
DLFTASNDPL  LWRFLYLRDF  RDNTVRVQDT  DWKELYRKRH  IQRKESPKGR  FVMLLPSSTH  420
TIPFYPNPLH  PRPFPSSRLP  PGIIGGEYDQ  RPTLPYVGDP  ISSLIPGPGE  TPSQFPPLRP  480
RFDPVGPLPG  PNPILPGRGG  PNDRFPFRPS  RGRPTDGRLS  FM                      522
```

Figure 2

MODULATORS OF THE FUNCTION OF RECEPTORS OF THE TNF/NGF RECEPTOR FAMILY AND OTHER PROTEINS

CROSS REFERENCE TO RELATED APPLICATION

The present application is a continuation-in-part of application Ser. No. 09/381,358, filed Sep. 20, 1999 now abandoned, which is a 371 national stage application of PCT/IL98/00125, filed Mar. 19, 1998, the entire contents of Ser. No. 09/381,358 being incorporated herein by reference.

FIELD OF THE INVENTION

The present invention is generally in the field of receptors belonging to the TNF/NGF superfamily of receptors and the control of their biological functions. The TNF/NGF superfamily of receptors includes receptors such as the p55 and p75 tumor necrosis factor receptors (TNF-Rs, hereinafter called p55-R and p75-R) and the FAS ligand receptor (also called FAS/APO1 or FAS-R and hereinafter will be called FAS-R) and others. Specifically, the present invention concerns novel proteins which bind to other proteins which themselves bind directly or indirectly to members of the TNF/NGF receptor family and other intracellular modulatory proteins, and more specifically, it relates to one such protein, herein designated RAP (for RIP-associated protein), which binds to RIP (for 'receptor interacting protein'), which, in turn, binds to itself and to MORT-1, FAS-R, p55-R, TRADD and Traf2.

Accordingly, the present invention concerns, in general, new proteins which are capable of modulating or mediating the function of RIP and thereby also capable of modulating or mediating, directly or indirectly, the function of other proteins which bind to RIP directly or indirectly. In particular, the present invention concerns RAP, its preparation and uses thereof, as well as any isoforms, analogs, fragments and derivatives of RAP, their preparation and uses.

DESCRIPTION OF THE RELATED ART

Tumor Necrosis Factor (TNF-α) and Lymphotoxin (TNF-β) (hereinafter, TNF, refers to both TNF-α and TNF-β) are multifunctional pro-inflammatory cytokines formed mainly by mononuclear phagocytes, which have many effects on cells (Wallach, D. (1986) In: *Interferon* 7 (Ion Gresser, ed.), pp. 83–222, Academic Press, London; and Beutler and Cerami (1987)). Both TNF-α and TNF-β initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that overproduction of TNF-α can play a major pathogenic role in several diseases. For example, effects of TNF-α, primarily on the vasculature, are known to be a major cause for symptoms of septic shock (Tracey et al., 1986). In some diseases, TNF may cause excessive loss of weight (cachexia) by suppressing activities of adipocytes and by causing anorexia, and TNF-α was thus called cachetin. It was also described as a mediator of the damage to tissues in rheumatic diseases (Beutler and Cerami, 1987) and as a major mediator of the damage observed in graft-versus-host reactions (Piquet et al., 1987). In addition, TNF is known to be involved in the process of inflammation and in many other diseases.

Two distinct, independently expressed, receptors, the p55 and p75 TNF-Rs, which bind both TNF-α and TNF-β specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Leotscher et al., 1990; Schall et al., 1990; Nophar et al., 1990; Smith et al., 1990; and Heller et al., 1990). However, the cellular mechanisms, for example, the various proteins and possibly other factors, which are involved in the intracellular signaling of the p55 and p75 TNF-Rs have yet to be elucidated. It is this intracellular signaling, which occurs usually after the binding of the ligand, i.e., TNF (α or β), to the receptor, that is responsible for the commencement of the cascade of reactions that ultimately result in the observed response of the cell to TNF.

As regards the above-mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al., 1992; Tartaglia et al., 1993) have shown that the biological function of the p55 TNF-R depends on the integrity of its intracellular domain, and accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer, and as such, has been suggested to induce intracellular signaling via the p55 TNF-R by way of its ability to bind to and to cross-link the receptor molecules, i.e., cause receptor aggregation.

Another member of the TNF/NGF superfamily of receptors is the FAS receptor (FAS-R) which has also been called the FAS antigen, a cell-surface protein expressed in various tissues and sharing homology with a number of cell-surface receptors including TNF-R and NGF-R. The FAS-R mediates cell death in the form of apoptosis (Itoh et al., 1991), and appears to serve as a negative selector of autoreactive T cells, i.e., during maturation of T cells, FAS-R mediates the apoptopic death of T cells recognizing self-antigens. It has also been found that mutations in the FAS-R gene (1pr) cause a lymphoproliferation disorder in mice that resembles the human autoimmune disease systemic lupus erythematosus (SLE) (Watanabe-Fukunaga et al., 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptopic cell death of the FAS-R-carrying cells. Further, monoclonal antibodies have been prepared that are specific for FAS-R, these monoclonal antibodies being capable of inducing apoptopic cell death in cells carrying FAS-R, including mouse cells transformed by cDNA encoding human FAS-R (Itoh et al., 1991).

A number of approaches have been made by the applicants (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by applicants (see for example EP 568925) have been made to modulate the TNF effect by modulating the activity of the TNF-Rs.

Briefly, EP 568925 relates to a method of modulating signal transduction and/or cleavage in TNF-Rs whereby peptides or other molecules may interact either with the receptor itself or with effector proteins interacting with the receptor, thus modulating the normal function of the TNF-Rs. In EP 568925, there is described the construction and characterization of various mutant p55 TNF-Rs, having mutations in the extracellular, transmembrane, and intracellular domains of the p55 TNF-R. In this way, regions within the above domains of the p55 TNF-R were identified as being essential to the functioning of the receptor, i.e., the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R, are also set forth in EP 568925. However, EP 568925 does not specify the actual proteins and peptides which bind to the intracellular domains of the TNF-Rs (e.g., p55 TNF-R), nor does it describe the yeast two-hybrid approach to isolate and identify such proteins or peptides which bind to the intracellular domains of TNF-Rs. Similarly, in EP 568925 there is no disclosure of proteins or peptides capable of binding the intracellular domain of FAS-R.

While it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al., 1992; Tartaglia et al., 1993; Itoh and Nagata, 1993). These regions (the 'death domains') have sequence similarity. The 'death domains' of both FAS-R and p55-R tend to self-associate. Their self-association apparently promotes that receptor aggregation which is necessary for initiation of signaling (see Song et al., 1994; Wallach et al., 1994; Boldin et al., 1995), and at high levels of receptor expression can result in triggering of ligand-independent signaling (Boldin et al., 1995).

Like other receptor-induced effects, cell death induction by the TNF receptors and FAS-R occurs via a series of protein-protein interactions, leading from ligand-receptor binding to the eventual activation of enzymatic effector functions, which in the case studies have elucidated non-enzymatic protein-protein interactions that initiate signaling for cell death : binding of trimeric TNF or the FAS-R ligand molecules to the receptors, the resulting interactions of their intracellular domains (Brakebusch et al., 1992; Tartaglia et al., 1993; Itoh and Nagata, 1993) augmented by a propensity of the death-domain motifs to self-associate (Boldin et al., 1995a), and induced binding of two cytoplasmic proteins (which can also bind to each other) to the receptors' intracellular domains—MORT-1 (or FADD) to FAS-R (Boldin et al., 1995b; Chinnaiyan et al., 1995; Kischkel et al., 1995) and TRADD to p55-R (Hsu et al., 1995; Hsu et al., 1996). Three proteins that bind to the intracellular domain of FAS-R and p55-R at the 'death domain' region involved in cell-death induction by the receptors through hetero-association of homologous regions and that independently are also capable of triggering cell death were identified by the yeast two-hybrid screening procedure. One of these is the protein, MORT-1 (Boldin et al. 1995b), also known as FADD (Chinnaiyan et al., 1995) that binds specifically to FAS-R. The second one, TRADD (see also Hsu et al., 1995, 1996), binds to p55-R, and the third, RIP (see also Stanger et al., 1995), binds to both FAS-R and p55-R. Besides their binding to FAS-R and p55-R, these proteins are also capable of binding to each other, which provides for a functional "cross-talk" between FAS-R and p55-R. These bindings occur through a conserved sequence motif, the 'death domain module' common to the receptors and their associated proteins. Furthermore, although in the yeast two-hybrid test MORT-1 was shown to bind spontaneously to FAS-R, in mammalian cells, this binding takes place only after stimulation of the receptor, suggesting that MORT-1 participates in the initiating events of FAS-R signaling. MORT-1 does not contain any sequence motif characteristic of enzymatic activity, and therefore, its ability to trigger cell death seems not to involve an intrinsic activity of MORT-1 itself, but rather, activation of some other protein(s) that bind MORT-1 and act further downstream in the signaling cascade. Cellular expression of MORT-1 mutants lacking the N-terminal part of the molecule has been shown to block cytotoxicity induction by FAS/APO1 (FAS-R) or p55-R (Hsu et al., 1996; Chinnaiyan et al., 1996), indicating that this N-terminal region transmits the signaling for the cytocidal effect of both receptors through protein-protein interactions.

Thus, the 'death domain' motifs of the receptors p55-R and FAS-R as well as their three associated proteins MORT-1, RIP and TRADD appear to be the sites of protein-protein interactions. The three proteins MORT-1, RIP and TRADD interact with the p55-R and FAS-R intracellular domains by the binding of their death domains to those of the receptors, and for both RIP and TRADD their death domains also self-associate, although MORT-1 differs in this respect in that its death domain does not self-associate. Further, MORT-1 and TRADD bind differentially to FAS-R and p55-R and also bind to each other. Moreover, both MORT-1 and TRADD bind effectively to RIP. Accordingly, it would seem that the interaction between the three proteins MORT-1, RIP and TRADD is an important part of the overall modulation of the intracellular signaling mediated by these proteins. Interference of the interaction between these three intracellular proteins will result in modulation of the effects caused by this interaction. For example, inhibition of TRADD binding to MORT-1 may modulate the FAS-R-p55 TNF-R interaction. Likewise, inhibition of RIP in addition to the above inhibition of TRADD binding to MORT-1 may further modulate FAS-R-p55 TNF-R interaction.

Monoclonal antibodies raised against the 'death domain' of p55-R, specifically against the binding site of sites of TRADD and RIP can also be used to inhibit or prevent binding of these proteins and thus cause modulation of the interaction between FAS-R and p55-R.

Moreover, it has also recently been found that besides the above noted cell cytotoxicity activities and modulation thereof mediated by the various receptors and their binding proteins including FAS-R, p55-R, MORT-1, TRADD, RIP, MACH, Mch4, and G1, a number of these receptors and their binding proteins are also involved in the modulation of the activity of the nuclear transcription factor NF-κB, which is a key mediator of cell survival or viability, being responsible for the control of expression of many immune- and inflammatory-response genes. For example, it has been found that TNF-α can actually stimulate activation of NF-κB and thus TNF-α is capable of inducing two kinds of signal in cells, one eliciting cell death and another that protects cells against death induction by inducing gene expression via NF-κB (see Beg and Baltimore, 1996; Wang et al., 1996; Van Antwerp et al., 1996). A similar dual effect for FAS-R has also been reported (see reference to this effect as stated in above Van Antwerp et al., 1996). It would therefore appear that there exists a delicate balance between cell death and cell survival upon stimulation of various types of cells with TNF-α and/or the FAS-R ligand, the ultimate outcome of the stimulation depending on which intracellular pathway is stimulated to a greater extent, the one leading to cell death (usually by apoptosis), or the one leading to cell survival via activation of NF-κB.

In addition, the present inventors have also recently further elucidated the possibly pathway by which members of the TNF/NGF receptor family activate NF-κB (see Malinin et al., 1997 and the various relevant references set forth therein; and co-owned, co-pending Israel Patent Application Nos. IL 117800 and IL 119133). Briefly, it arises that several members of the TNF/NGF receptor family are capable of activating NF-κB through a common adaptor protein, Traf2. A newly elucidated protein kinase called NIK (see above Malinin et al., 1997 and IL 117800 and IL 119133) is capable of binding to Traf2 and of stimulating NF-κB activity. In fact, it was shown (see aforesaid Malinin et al. and IL applications) that expression in cells of kinase-deficient NIK mutants results in the cells being incapable of having stimulation of NFκB in a normal endogenous manner and also in the cell having a block in induction of NF-κB activity by TNF, via either FAS-R, and a block in NF-κB induction by TRADD, RIP and MORT-1 (which are adaptor proteins that bind these p55-R and/or FAS-R receptors). All of the receptors p55-R, p75-R, FAS-R and their adaptor proteins MORT-1, TRADD and RIP bind directly or indirectly to Traf2, which by its binding ability to NIK apparently modulates the induction of NF-κB.

Of the above modulator proteins involved in the fine balance between cell death and survival following stimulation of FAS-R and/or p55-R, the protein RIP appears to have an important role. RIP (see Stanger et al., 1995 and also Malinin et al., 1997) has a 'death domain' in its C-terminal region which enables it to induce cell cytotoxicity in an independent way and also by association with th death domains of MORT-1, p55-R, FAS-R and TRADD. RIP also has a protein kinase domain at its N-terminal region and an intermediate domain which is believed to enable its intersection (binding) with Traf2 and thereby its involvement in NF-κB induction. Accordingly, details concerning the characteristics and sequences (DNA and amino acid) of RIP are set forth in the above noted publications (in particular, Stanger et al., 1995) which are incorporated herein in their entirety by reference.

The clone of about 2.2 kB, from which the DNA sequence encoding the RAP protein according to the present invention, as presented in patent application Ser. No. 09/381,358, filed Sep. 20, 1999, which is a 371 national stage of PCT/IL98/00125, filed Mar. 19, 1998, was obtained, was resequenced. The laboratory of the present inventors discovered upon resequencing this clone that the originally obtained cDNA encoding the RAP protein was not correctly sequenced. Accordingly, both the DNA and the amino acid sequences of RAP protein, which are resequenced and deduced, respectively, and which are inherent from the same deposited clone of about 2.2 kB, are disclosed herein and are entitled to the benefit of priority based on the deposit of the clone of about 2.2 kB which was originally sequenced.

SUMMARY OF THE INVENTION

It is an object of the invention to provide a novel protein RAP, including all isoforms, analogs, fragments or derivatives thereof, capable of binding to the RIP protein (herein after 'RIP'). As RIP is capable of interacting directly or indirectly with the intracellular mediators of inflammation, cell cytotoxicity/cell death, such as p55-R and FAS-R and their associated adaptor or modulator proteins such as, for example, MORT-1, TRADD, MACH, Mch4, G1 and others, the novel proteins of the present invention by binding to RIP are therefore capable of affecting the intracellular signaling process initiated by the binding of the FAS ligand to its receptor, and TNF to its receptor (p55-R), and as such the new proteins of the present invention are modulators of the p55-R and FAS-R-mediated effect on cells. As RIP is also capable of interacting with Traf2 and thereby is capable of interacting directly or indirectly with NIK and as such RIP acts as a modulator of inflammation and of cell survival pathways involving NF-κB induction, and hence the new proteins of the present invention are modulators of RIP-related inflammation and cell survival activity. Likewise, by way of the FAS-R, p55-R and their modulator proteins MORT-1 and TRADD being capable of inducing NF-κB and cell survival either directly or indirectly by binding to RIP or by binding to Traf2, to which RIP binds the proteins of the present invention may also be mediators or cell survival processes by way of operating via common or related intracellular signaling pathways in which the various above proteins operate to induce cell survival. Similarly, as p75-R binds to Traf2 to which RIP binds, the novel proteins of the invention may also be modulators of RIP-related mediation of p75-R mediated activity.

Another object of the invention is to provide antagonists (e.g., antibodies, peptides, organic compounds, or even some isoforms) to the above novel RAP proteins, isoforms, analogs, fragments and derivatives thereof, which may be used to inhibit the signaling process, or, more specifically, the inflammation cell-cytotoxicity, or cell-survival processes, when desired.

A further object of the invention is to use the above novel RAP proteins, isoforms, analogs, fragments and derivatives thereof, to isolate and characterize additional proteins or factors, which may be involved in regulation of receptor activity, e.g., other proteins which may bind to RAP proteins and influence their activity, and/or to isolate and identify other receptors further upstream or downstream in the signaling process(es) to which these novel proteins, analogs, fragments and derivatives bind, and hence, in whose function they are also involved.

A still further object of the invention is to provide inhibitors which can be introduced into cells to bind or interact with RAP and possible RAP isoforms which inhibitors may act to inhibit RIP-associated activity in cell cytotoxic processes and hence, when desired, to enhance cell survival, or which may act to inhibit RIP-associated activity in cell-survival processes and hence, when desired, to enhance cell cytotoxicity.

Moreover, it is an object of the present invention to use the above-mentioned novel RAP proteins, isoforms and analogs, fragments and derivatives thereof as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g., for identifying disorders related to abnormal functioning of cellular effects mediated by the p55-R, FAS-R or other related receptors.

A further object of the invention is to provide pharmaceutical compositions comprising the above novel RAP proteins, isoforms, or analogs, fragments or derivatives thereof, as well as pharmaceutical compositions comprising the above noted antibodies or other antagonists.

In accordance with the present invention, a novel protein RAP has been isolated. RAP is capable of binding to, or interacting with, RIP, and hence is a modulator or mediator of RIP intracellular activity. RIP is involved in the modulation or mediation of intracellular signaling pathways, e.g. the cell cytotoxicity or cell death associated pathway in which RIP has cytotoxic activity by itself and in association, directly or indirectly, with a number of other cell-death associated proteins, such as, for example, MORT-1, TRADD, MACH, Mch4, G1, p55-R and FAS-R, with which RIP can associate or bind to in a direct or indirect fashion via the 'death domain' motif/module present in RIP and in all the aforesaid proteins; another pathway being the inflammation, cell survival or viability pathway in which RIP may have an activation role, directly or indirectly by virtue of the presence of a kinase motif or domain present in RIP and RIP's ability to be capable of binding to Traf2 which can bink NIK which, in turn, is directly involved in activation of NF-κB which plays a central role in inflammation and cell survival. Further, p55-R and TRADD are also capable of interaction with Traf2 and are also implicated in NF-κB activation and thereby in the cell survival pathway, and hence RIP by being capable of binding to or interacting with p55-R, FAS-R and TRADD (as well as Traf2) may also be implicated in the modulation of inflammation, cell survival activation by these proteins. Accordingly, RIP is a modulator or mediator of these pathways, and likewise, the new RAP of the present invention by binding to RIP is a modulator or mediator of these intracellular pathways.

RAP has been isolated and cloned using the yeast two-hybrid system, sequenced and characterized, and as is detailed herein below, RAP appears to be a highly specific RIP-binding protein and hence a specific RIP modulator/mediator. RAP does not bind to TRADD, MORT-1, p55-R, p75-R and MACH. Further, it appears that RAP does not have a characteristic death domain module or motif, this being consistent with the finding that RAP does not induce cell cytotoxicity on its own.

As will be used herein throughout, RIP activity is meant to include both its activity in modulation/mediation in the inflammation and cell death/survival pathway and its activity in the modulation/mediation of the cell survival pathway. These activities are indicated hereinabove and hereinbelow as well as in all the above-mentioned publications and patent applications, the full contents of which are incorporated herein by reference. Likewise, as used herein throughout RAP activity is meant to include its modulation/mediation of RIP activity by virtue of its specific binding to RIP, this modulation/mediation of RIP by RAP including modulation/mediation of the inflammation, cell death and cell survival pathways in which RIP is involved directly or indirectly, and as such RAP may be considered as an indirect modulator/mediator of all the above mentioned proteins and possibly a number of others which are involved in inflammation, cell death or cell survival and to which RIP binds, or with which RIP interacts in a direct or indirect fashion.

Thus, in accordance with the present invention, a new protein designated RAP is provided. As noted above, RAP was isolated and cloned by the two-hybrid screening assay and characterized as a molecule which binds RIP. Sequencing of RAP has revealed that it is a novel protein as sequence comparisons performed between the RAP sequence and those in the various databases, for example, Genebank 'dbest' and Human Genome Database level 1 databases, did not show any apparent homology between RAP sequences and any known sequences. Actually two DNA sequences, differing only in their 5'-non coding regions were found, probably arising from the same gene by alternative splicing.

It still remains to be elucidated how RAP binds to RIP, in particular, there needs to be determined the homology or binding regions between RAP and RIP which permit their binding to each other. RAP apparently does not have a death domain module nor any other known region of enzymatic or other activity, for example, a kinase or protease domain.

In view of the above-mentioned, it therefore arises, as noted above and as set forth hereinbelow, that RAP is apparently a specific RIP-binding protein and hence a modulator/mediator of RIP intracellular activity.

Thus, as RAP apparently has a role in modulating/mediating inflammation, cell survival and/or cell death activities in which RIP is involved directly or indirectly especially those related to cytotoxicity and inflammation caused or induced by various stimuli including those transmitted via receptors of the TNF/NGF receptor family and possibly others as well. (For a scheme of RIP's involvement in these intracellular events and hence RAP's involvement, see FIG. 1 in Malinin et al., 1997).

RAP may also serve as an inhibitor of cell cytotoxicity and inflammation by virtue of its being present as part of a complex of other proteins, e.g. RIP and proteins bound to RIP, and as such may affect the cytotoxicity or inflammatory effects of these other proteins (e.g. p55-R, FAS-R, MACH, Mch4, G1 and MORT-1), ultimately resulting in an inhibition of their cytotoxic activity or their activity in inflammation.

RAP may yet also serve as an enhancer or augmentor of cell cytotoxicity and inflammation and this by augmenting the activity of other proteins, e.g. RIP and other proteins bound to RIP as noted above aiding in the recruitment of these proteins by RIP, the recruitment serving to augment the cytotoxic activity of the various proteins or to augment their inflammatory effects.

Likewise, in an analogous fashion RAP may also serve as an inhibitor or an augmentor of the cell-survival pathway as noted above by virtue of RIP's involvement in this pathway.

Accordingly, the present invention provides a DNA sequence encoding a RIP-associated protein (RAP) isoforms, analogs or fragments thereof, capable of binding to RIP and modulating or mediating the intracellular activity of RIP, said intracellular activity being a modulation/mediation of inflammation and/or cell death and/or cell survival.

In particular, the present invention provides a DNA sequence selected from the group consisting of:

(a) a cDNA sequence derived from the coding region of a native RAP protein;

(b) DNA sequences capable of hybridization to a sequence of (a) under moderately stringent conditions and which encode a biologically active RAP protein; and (c) DNA sequences which are degenerate as a result of the genetic code to the DNA sequences defined in (a) and (b) and which encode a biologically active RAP protein.

Another specific embodiment of the above DNA sequence of the invention is a DNA sequence comprising at least part of the sequence encoding at least one isoform of the RAP protein. Another embodiment of the above DNA sequence is the sequence encoding the RAP protein as depicted in FIG. 1 (SEQ ID NO:1).

The present invention provides RAP proteins, and analogs, fragments or derivatives thereof encoded by any of the above sequences of the invention, said proteins, analogs, fragments and derivatives being capable of binding to RIP and modulating/mediating its biological activity in cell death and/or cell survival pathways intracellularly.

A specific embodiment of the invention is the RAP protein, analogs, fragments and derivatives thereof. The RAP protein sequence as deduced from the DNA sequence of FIG. 1 is shown in FIG. 2 (SEQ ID NO:2). Another embodiment is any isoform of the RAP protein, analogs, fragments and derivatives thereof.

Also provided by the present invention are vectors encoding the above RAP protein, and analogs, fragments or derivatives of the invention, which contain the above DNA sequence of the invention, these vectors being capable of being expressed in suitable eukaryotic or prokaryotic host cells; transformed eukaryotic or prokaryotic host cells containing such vectors; and a method for producing the RAP protein, or analogs, fragments or derivatives of the invention by growing such transformed host cells under conditions suitable for the expression of said protein, analogs, fragments or derivatives, effecting post-translational modifications of said protein as necessary for obtaining said protein and extracting said expressed protein, analogs, fragments or derivatives from the culture medium of said transformed cells or from cell extracts of said transformed cells. The above definitions are intended to include all isoforms of the RAP protein.

In another aspect, the present invention also provides antibodies or active derivatives or fragments thereof specific for the RAP protein, and analogs, fragments and derivatives thereof, of the invention.

By yet another aspect of the invention, there are provided various uses of the above DNA sequences or the proteins which they encode, according to the invention, which uses include amongst others:

(i) A method for the modulation of the intracellular inflammation, cell death and/or cell survival pathways modulated or mediated by the protein RIP, comprising treating said cells with one or more RAP proteins, isoforms, analogs, fragments or derivatives thereof, capable of binding to RIP wherein said treating of said cells comprises introducing into said cells said one or more proteins, isoforms, analogs, fragments or derivatives thereof in a form suitable for intracellular introduction thereof, or introducing into said cells a DNA sequence encoding said one or more proteins, isoforms, analogs, fragments or derivatives in the form of a suitable vector carrying said sequence, said vector being capable of effecting the insertion of said sequence into said cells in a way that said sequence is expressed in said cells.

(ii) A method for the modulation of the inflammation, cell death and/or cell survival pathways mediated by ligands of the TNF family by effect on cells via the action of the RIP protein, according to (i) above, wherein said treating of cells comprises introducing into said cells said RAP protein, or isoforms, analogs, fragments or derivatives thereof, in a form suitable for intracellular introduction, or introducing into said cells a DNA sequence encoding said G1 protein, or isoforms, analogs, fragments or derivatives in the form of a suitable vector carrying said sequence, said vector being capable of effecting the insertion of said sequence into said cells in a way that said sequence is expressed in said cells.

(iii) A method as in (ii) above wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of a FAS-R- or p55-R-carrying cell and a second sequence encoding a protein selected from RAP protein, and isoforma, analogs, fragments and derivatives thereof, that when expressed in said cells is capable of modulating/mediating the intracellular inflammation, cell death and/or cell survival pathways; and (b) infecting said cells with said vector of (a).

(iv) A method for modulating the inflammation, cell death and/or cell survival pathways mediated by the ligands of the TNF family effect on cells via the action of the RIP protein comprising treating said cells with antibodies or active fragments or derivatives thereof, according to the invention, said treating being by application of a suitable composition containing said antibodies, active fragments or derivatives thereof to said cells, wherein when at least part of the RAP protein is exposed on the extracellular surface, said composition is formulated for extracellular application, and when said RAP proteins are entirely intracellular, said composition is formulated for intracellular application.

(v) A method for modulating the inflammation, cell death and/or cell survival pathways mediated by the ligands of the TNF family effect on cells via the action of the RIP protein comprising treating said cells with an oligonucleotide sequence encoding an antisense sequence of at least part of the RAP protein sequence of the invention, said oligonucleotide sequence being capable of blocking the expression of the RAP protein.

(vi) A method as in (ii) above for treating tumor cells or HIV-infected cells or other diseased cells, comprising:

(a) constructing a recombinant animal virus vector carrying a sequence encoding a viral surface protein capable of binding to a specific tumor cell surface receptor or HIV-infected cell surface receptor or receptor carried by other diseased cells and a sequence encoding a protein selected from RAP protein, analogs, fragments and derivatives of the invention, that when expressed in said tumor, HIV-infected, or other diseased cell is capable of killing said cell via the action of the RAP protein; and (b) infecting said tumor or HIV-infected cells or other diseased cells with said vector of (a).

(vii) A method for modulating the cell death and/or cell survival pathways mediated by ligands of the TNF family effect on cells via the action of the RIP protein comprising applying the ribozyme procedure in which a vector encoding a ribozyme sequence capable of interacting with a cellular mRNA sequence encoding a RAP protein according to the invention, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said RAP protein in said cells.

(viii) A method selected from the above methods according to the invention, wherein said RAP protein encoding sequence comprises at least one of the RAP isoforms, analogs, fragments and derivatives of any thereof according to the invention which are capable of binding to RIP.

(ix) A method for isolating and identifying proteins, according to the invention capable of binding to the RIP protein, comprising applying the yeast two-hybrid procedure in which a sequence encoding said RIP protein or is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said RIP protein.

(x) A method according to any of the (i)–(ix) above wherein said RAP protein is any one of the isoforms of RAP, analogs, fragments and derivatives of any thereof.

(xi) A method according to any of the above (i)–(x) wherein the RAP protein or any of its isoforms, analogs, fragments or derivatives is involved in the modulation of the cellular effect mediated or modulated by any other mediator or inducer to which said RAP protein, isoform, analog, fragment or derivative is capable of binding directly or indirectly.

The present invention also provides a pharmaceutical composition for the modulation of inflammation, the cell death and/or cell survival pathways mediated by the TNF family effect on cells via the action of the RIP protein or the effect of any other mediator or inducer on cells as noted above, comprising, as active ingredient any one of the following:

(i) a RAP protein according to the invention, and biologically active fragments, analogs, derivatives of mixtures thereof;

(ii) a recombinant animal virus vector encoding a protein capable of binding a cell surface receptor and encoding a RAP protein or biologically active fragments or analogs, according to the invention;

(iii) an oligonucleotide sequence encoding an anti-sense sequence of the RAP protein sequence according to the invention, wherein said oligonucleotide may be the second sequence of the recombinant animal virus vector of (ii) above.

The present invention also provides:

I. a method for the modulation of the inflammation, intracellular cell death and/or cell survival pathways modulated/mediated by the RIP protein, or the effect of any other mediator or inducer, or any other NF-κB inducer or inhibitor, on cells comprising treating said cells in accordance with a method of any one of (i)–(x) above, with RAP proteins, isoforms, analogs, fragments or derivatives thereof or with sequences encoding RAP proteins, isoforms, analogs or fragments thereof, said treatment resulting in the enhancement or inhibition of said RIP-mediated effect, and thereby also of the FAS-R or p55-R-mediated effect, or of said other mediator or inducer, or other NF-κB inducer or inhibitor.

II. a method as above wherein said RAP protein, analog, fragment or derivative thereof is that part of the RAP protein which is specifically involved in binding to RIP, or said other mediator or inducer, or other NF-κB inducer or inhibitor, or said RAP protein sequence encodes that part of RAP protein which is specifically involved in binding to RIP, or said other mediator or inducer, or other NF-κB inducer or inhibitor.

III. a method as above wherein said RAP protein is any one of the RAP isoforms, said isoforms capable of enhancing the RIP-associated effect.

IV. a method as above wherein said RAP protein is any one of the RAP isoforms, said isoforms capable of inhibiting the RIP-associated effect, or other mediator or inducer associated effect on cells and thereby also of inhibiting the FAS-R- or p55-R-associated effect on cells, or the other cytotoxic mediator or inducer effect on cells.

V. a method as above wherein said RAP protein, isoform, analog, fragment or derivative capable of enhancing or inhibiting the RIP-associated effect on the inflammation and cell survival pathway by way of direct or indirect inhibition of NF-κB, or direct or indirect activation of JNK or p38 kinase.

Isolation of the RAP proteins, their identification and characterization may be carried out by any of the standard screening techniques used for isolating and identifying proteins, for example, the yeast two-hybrid method, affinity chromatography methods, and any of the other well-known standard procedures used for this purpose.

Other aspects and embodiments of the present invention are also provided as arising from the following detailed description of the invention.

It should be noted that, where used throughout, the following terms: "Modulation/Mediation of the RIP, or FAS-ligand, or TNF effect on cells"; and any other such "Modulation/Mediation" mentioned in the specification are understood to encompass in vitro as well as in vivo treatment and, in addition, also to encompass inhibition or enhancement/augmentation.

BRIEF DESCRIPTION OF THE DRAWINGS

FIG. 1 shows the nucleotide sequence of RAP (SEQ ID NO:1) with the ATG initiation codon and the TGA step codon indicated in bold.

FIG. 2 shows the deduced amino acid sequence of RAP (SEQ ID NO:2).

DETAILED DESCRIPTION OF THE INVENTION

The present invention relates, in one aspect, to novel RAP proteins which are capable of binding to the RIP protein and thereby of mediating or modulating the intracellular activity of RIP especially where RIP is involved in modulation or mediation of inflammation, the cell death and/or cell survival pathways as detailed herein above. Thus RAP may inhibit RIP activity in the cell death/inflammation survival pathway, RAP may enhance RIP activity in the inflammation or cell death survival pathway, or it may enhance RIP activity in one of these pathways while inhibiting it in the other.

More particularly, in accordance with the present invention, a new protein RAP is provided. RAP has been sequenced and characterized and it was found that RAP is a RIP-binding protein having high specificity for RIP, but does not show binding towards a number of proteins known to be involved in the intracellular signaling pathways which lead to inflammation, cell death or to cell survival. RAP also apparently has none of the domains common to proteins which are active in either of these pathways, i.e. RAP does not have a 'death domain' motif or module, it does not have a kinase motif or domain and it does not have a protease domain or motif. The RAP sequence determined is also a unique sequence as arises from a comparison with sequences in a number of databases including the Genebank, Human Genome level 1 and 'dbest' databases. As detailed above (also with reference to all publications and patent applications as noted) RIP is involved in the inflammation, cell death and cell survival pathways intracellularly. Hence, regulation or control of the activity of RIP can regulate either or all of these pathways when such pathways are initiated, by for example, the binding of TNF or Fas-ligand to their receptors (for TNF, the p55-R in particular). RIP may play a key role in determining which pathway is activated to a greater extent and this by virtue of its being able to bind a number of cytotoxic proteins having death domains and also a number of proteins having kinase activity. Accordingly, proteins, such as the RAP protein of the present invention, which can bind specifically to RIP may play an important role in modulating RIP activity and thereby modulating the extent of induction of the one pathway in comparison to the others. Thus, the RAP protein of the present invention represents an important intracellular signal modulator or mediator.

Due to the unique ability of FAS-R and the TNF receptors to cause cell death, as well as the ability of the TNF receptors to trigger various other tissue-damaging activities, aberration of the function of these receptors can be particularly deleterious to the organism. Indeed, both excessive and deficient function of these receptors have been shown to contribute to the pathological manifestations of various diseases. Identifying molecules that take part in the signaling activity of these receptors, and finding ways to modulate the function of these molecules, constitutes a potential clue for new therapeutical approaches to these diseases. In view of the suspected important role of RIP in FAS-R and p55-R toxicity, and hence the suspected important regulatory role of RAP in FAS-R and TNF via modulation of RIP, it seems particularly important to design drugs that can block the cytotoxic function of RIP, possibly by way of blocking the binding of RAP to RIP or otherwise inhibiting the interaction between RAP and RIP under those conditions in which RAP serves to enhance RIP-mediated cytotoxicity (as noted above RIP is cytotoxic on its own and in conjunction with other proteins have death domain regions).

Likewise, it is also known (see above) that FAS-R and p55-R are involved in the activation of NF-κB and thereby of cell survival. Accordingly, when it is desired to kill cells, for example cancer cells, HIV-infected cells and the like, it would be desirable to enhance the cytotoxic effects of FAS-R and p55-R (and their associated proteins such as, for example, MORT-1, MACH, Mch4, G1, TRADD), while at the same time to inhibit their ability to induce NF-κB. Hence, when the RAP interaction or binding to RIP results in an augmentation of RIP's possible role in enhancing NF-κB induction (possibly via Traf2 and possibly via the kinase domain and/or intermediate domain of RIP), then it would be desirable to block this interaction between RAP and RIP to inhibit, or at least to prevent augmentation, of NF-κB activation and thereby shift the balance of TNF- or FAS-ligand-induced effects to the side of cell cytotoxicity to ultimately provide for increased cell death.

Similarly, in the opposite situation (to that noted above) where RAP's binding to RIP actually causes inhibition of FAS-R and p55-R inflammatory or cytotoxic effects and it is desired to block these cytotoxic effects, e.g. in inflammation, various autoimmune diseases and the like where increased cell survival is sought, then it is important to design drugs which would enhance the interaction between RAP and RIP to enhance the overall inhibition of cell death and shift the balance towards cell survival. It also follows in light of the above that in the event that RAP's interaction with RIP causes an inhibition in RIP's function in augmenting NF-κB activation, then when cell survival is desired, it is necessary to block this interaction between RAP and RIP thereby enhancing RIP's activity in augmenting NF-κB activation.

In view of all of the aforementioned, it arises that RIP has a key role in the balance between induction or mediation of inflammation, cell death or cell survival pathways and hence RAP has an equally important role by being a modulator of RIP. Influencing the RAP-RIP interaction/binding using various drugs or treatments as noted above and below will possibly allow for a shift in the intracellular signaling pathways from cell death to cell survival or vice versa as is desired.

The present invention also concerns the DNA sequence encoding a RAP protein and the RAP proteins encoded by the DNA sequences.

Moreover, the present invention further concerns the DNA sequences encoding biologically active analogs, fragments and derivatives of the RAP protein, and the analogs, fragments and derivatives encoded thereby. The preparation of such analogs, fragments and derivatives is by standard procedure (see for example, Sambrook et al., 1989) in which in the DNA sequences encoding the RAP protein, one or more codons may be deleted, added or substituted by another, to yield analogs having at least one amino acid residue change with respect to the native protein.

Of the above DNA sequences of the invention which encode a RAP protein, isoform, analog, fragment or derivative, there is also included, as an embodiment of the invention, DNA sequences capable of hybridizing with a cDNA sequence derived from the coding region of a native RAP protein, in which such hybridization is performed under moderately stringent conditions, and which hybridizable DNA sequences encode a biologically active RAP protein. These hybridizable DNA sequences therefore include DNA sequences which have a relatively high homology to the native RAP cDNA sequence and as such represent RAP-like sequences which may be, for example, naturally-derived sequences encoding the various RAP isoforms, or naturally-occuring sequences encoding proteins belonging to a group of RAP-like sequences encoding a protein having the activity of RAP. Further, these sequences may also, for example, include non-naturally occuring, synthetically produced sequences, that are similar to the native RAP cDNA sequence but incorporate a number of desired modifications. Such synthetic sequences therefore include all of the possible sequences encoding analogs, fragments and derivatives of RAP, all of which have the activity of RAP.

To obtain the various above noted naturally occurring RAP-like sequences, standard procedures of screening and isolation of naturally-derived DNA or RNA samples from various tissues may be employed using the natural RAP cDNA or portion thereof as probe (see for example standard procedures set forth in Sambrook et al., 1989).

Likewise, to prepare the above noted various synthetic RAP-like sequences encoding analogs, fragments or derivatives of RAP, a number of standard procedures may be used as are detailed herein below concerning the preparation of such analogs, fragments and derivatives.

A polypeptide or protein "substantially corresponding" to RAP protein includes not only RAP protein but also polypeptides or proteins that are analogs of RAP.

Analogs that substantially correspond to RAP protein are those polypeptides in which one or more amino acid of the RAP protein's amino acid sequence has been replaced with another amino acid, deleted and/or inserted, provided that the resulting protein exhibits substantially the same or higher biological activity as the RAP protein to which it corresponds.

In order to substantially correspond to RAP protein, the changes in the sequence of RAP proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to RAP proteins, one such technique is the use of conventional mutagenesis techniques on the DNA encoding the protein, resulting in a few modifications. The proteins expressed by such clones can then be screened for their ability to bind to RIP and to modulate RIP activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of RAP proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of RAP protein.

TABLE IA

| Original Residue | Exemplary Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of RAP protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3–9 of Creighton, T. E., Proteins: Structure and Molecular Properties, W. H. Freeman & Co., San Francisco, Calif. 1983. Based on such an analysis, alternative conservative substitutions are defined herein as exchanges within one of the following five groups:

TABLE IB

| | |
| --- | --- |
| 1. | Small aliphatic, nonpolar or slightly polar residues: Ala, Ser, Thr (Pro, Gly); |
| 2. | Polar negatively charged residues and their amides: Asp, Asn, Glu, Gln; |
| 3. | Polar, positively charged residues: His, Arg, Lys; |
| 4. | Large aliphatic nonpolar residues: Met, Leu, Ile, Val (Cys); and |
| 5. | Large aromatic residues: Phe, Tyr, Trp. |

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain and generally tends to promote β-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. a-helix or β-sheet, as well as changes in biological activity, e.g., binding to RIP and/or mediation of RIP's effect on cell death.

Examples of production of amino acid substitutions in proteins which can be used for obtaining analogs of RAP proteins for use in the present invention include any known method steps, such as presented in U.S. Pat. RE 33,653, U.S. Pat. Nos. 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of RAP protein, either conservative substitutions or less conservative and more random changes, which lead to an increase in biological activity of the analogs of RAP proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable RAP analogs are those which retain at least the capability of binding to RIP, and thereby, as noted above mediate the activity of RIP in the intracellular pathways as noted above. In such a way, analogs can be produced which have a so-called dominant-negative effect, namely, an analog which is defective either in binding to RIP, or in subsequent signaling or other activity following such binding. Such analogs can be used, for example, to inhibit the effect of RIP, or to inhibit the NF-κB inducing (direct or indirect) effect of RIP, depending on which of these activities is the major one modulated by the interaction of RAP and RIP (see above), and this by such analogs competing with the natural RAP for binding to RIP.

At the genetic level, these analogs are generally prepared by site-directed mutagenesis of nucleotides in the DNA encoding the RAP protein, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., Current Protocols in Molecular Biology, Greene Publications and Wiley Interscience, New York, N.Y., 1987–1995; Sambrook et al., Molecular Cloning: A Laboratory Manual, Cold Spring Harbor Laboratory, Cold Spring Harbor, N.Y., 1989.

Preparation of a RAP protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a RAP protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated RAP protein sequence may be removed and placed in an appropriate vector, generally a transfer or expression vector of the type that may be employed for transfection of an appropriate host.

Accordingly, gene or nucleic acid encoding for a RAP protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding RAP protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; U.S. Pat. Nos. 4,795,699 and 4,921,794 to Tabor et al.; U.S. Pat. No. 5,142,033 to Innis; U.S. Pat. No. 5,122,464 to Wilson et al.; U.S. Pat. No. 5,091,310 to Innis; U.S. Pat. No. 5,066,584 to Gyllensten et al.; U.S. Pat. No. 4,889,818 to Gelfand et al.; U.S. Pat. No. 4,994,370 to Silver et al.; U.S. Pat. No. 4,766,067 to Biswas; U.S. Pat. No. 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

In an analogous fashion, biologically active fragments of RAP proteins (e.g. those of any of the RAP or its isoforms) may be prepared as noted above with respect to the analogs of RAP proteins. Suitable fragments of RAP proteins are those which retain the RAP capability and which can modulate or mediate the biological activity of RIP or other proteins associated with RIP directly or indirectly. Accordingly, RAP protein fragments can be prepared which have a dominant-negative or a dominant-positive effect as noted above with respect to the analogs. It should be noted that these fragments represent a special class of the analogs of the invention, namely, they are defined portions of RAP proteins derived from the full RAP protein sequence (e.g., from that of any one of the RAP or its isoforms), each such portion or fragment having any of the above-noted desired activities. Such fragment may be, e.g., a peptide.

Similarly, derivatives may be prepared by standard modifications of the side groups of one or more amino acid residues of the RAP protein, its analogs or fragments, or by conjugation of the RAP protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as RAP proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

RAP is a protein or polypeptide, i.e. a sequence of amino acid residues. A polypeptide consisting of a larger sequence which includes the entire sequence of a RAP protein, in accordance with the definitions herein, is intended to be included within the scope of such a polypeptide as long as the additions do not affect the basic and novel characteristics of the invention, i.e., if they either retain or increase the biological activity of RAP protein or can be cleaved to leave a protein or polypeptide having the biological activity of RAP protein. Thus, for example, the present invention is intended to include fusion proteins of RAP protein with other amino acids or peptides.

The new RAP protein, their analogs, fragments and derivatives thereof, have a number of possible uses, for example:

(i) RAP protein, its analogs, fragments and derivatives thereof, may be used to modulate the function of RIP in either of the inflammation, cell death or the cell survival pathways as noted above. For example, if RAP can modulate RIP's effect on activation of NF-κB, JNK (June kinase) or p38 kinase, both such RAP effects leading to enhance such a RAP-RIP effect when it would be desirable in anti-tumor, anti- or pro-inflammatory, anti-HIV applications, etc. In this case the RAP protein, its analogs, fragments or derivatives thereof, which modulate inflammation, enhance the cytotoxic effect, or block the cell survival effect, may be introduced to the cells by standard procedures known per se. For example, when the RAP protein is entirely intracellular (as suspected) and should be introduced only into the cells where the FAS-R ligand or TNF or other cytotoxic protein effect, mediated by RIP, is desired, a system for specific introduction of this protein into the cells is necessary. One way of doing this is by creating a recombinant animal virus, e.g., one derived from Vaccinia, to the DNA of which the following two genes will be introduced: the gene encoding a ligand that binds to cell surface proteins specifically expressed by the cells, e.g., ones such as the AIDs (HIV) virus gp120 protein which binds specifically to some cells (CD4 lymphocytes and related leukemias), or any other ligand that binds specifically to cells carrying a FAS-R or p55-R, such that the recombinant virus vector will be capable of binding such FAS-R- or p55-R -carrying cells; and the gene encoding the RAP protein. Thus, expression of the cell-surface-binding protein on the surface of the virus will target the virus specifically to the tumor cell or other FAS-R- or p55-R-carrying cell, following which the RAP protein encoding sequence will be introduced into the cells via the virus, and once expressed in the cells, will result in enhancement of the RIP mediation of the FAS-R ligand or TNF effect or independent RIP. Construction of such recombinant animal virus is by standard procedures (see for example, Sambrook et al., 1989). Another possibility is to introduce the sequences of the RAP protein (e.g., any one of the RAP or its isoforms) in the form of oligonucleotides which can be absorbed by the cells and expressed therein.

(ii) They may be used to inhibit the FAS-R ligand or TNF or related protein effect, mediated by RIP or independent RIP effect, e.g., in cases such as tissue damage in septic shock, graft-vs.-host rejection, or acute hepatitis, in which it is desired to block the FAS-R ligand or TNF induced FAS-R or p55-R intracellular signaling or independent RIP effect, or other protein-mediated signaling and at the same time to increase the cell survival pathway. In this situation, it is possible, for example, to introduce into the cells, by standard procedures, oligonucleotides having the anti-sense coding sequence for the RAP protein, which would effectively block the translation of mRNAs encoding the RAP protein and thereby block its expression and lead to the inhibition of the FAS-R ligand- or TNF- or RIP or other protein-effect. Such oligonucleotides may be introduced into the cells using the above recombinant virus approach, the second sequence carried by the virus being the oligonucleotide sequence.

Likewise, as noted above, depending on the nature of the RAP-RIP interaction, it may be possible by the ways of (i) and (ii) above to enhance or inhibit cell inflammation and survival pathways where desired.

Another possibility is to use antibodies specific for the RAP protein to inhibit its intracellular signaling activity.

Yet another way of inhibiting the RIP-mediated effects or RIP independent effect is by the recently developed ribozyme approach. Ribozymes are catalytic RNA molecules that specifically cleave RNAs. Ribozymes may be engineered to cleave target RNAs of choice, e.g., the mRNAs encoding the RAP protein of the invention. Such ribozymes would have a sequence specific for the RAP protein mRNA and would be capable of interacting therewith (complementary binding) followed by cleavage of the mRNA, resulting in a decrease (or complete loss) in the expression of the RAP protein, the level of decreased expression being dependent upon the level of ribozyme expression in the target cell. To introduce ribozymes into the cells of choice (e.g., those carrying FAS-R or p55-R), any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993; Shore et al., 1993; Joseph and Burke, 1993; Shimayama et al., 1993; Cantor et al., 1993;

Barinaga, 1993; Crisell et al., 1993 and Koizumi et al., 1993). This approach is suitable when the RAP-RIP interaction enhances cell cytotoxicity in situations when it is desired to block this cytotoxicity, or when the RAP-RIP interaction inhibits NF-κB activation in the same situation when it is desired to block this inhibition to increase such NF-κB activation, i.e. in both cases it is desired to increase cell survival as in (ii) above.

(iii) The RAP protein, its analogs, fragments or derivatives may also be used to isolate, identify and clone other proteins of the same class, i.e., those binding to RIP or to functionally related receptors or proteins, involved in the intracellular signaling process. In this application the above noted yeast two-hybrid system may be used, or there may be used a recently developed system employing non-stringent Southern hybridization followed by PCR cloning (Wilks et al., 1989). In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the RAP protein to identify and clone those of related RIP-binding proteins.

(iv) Yet another approach to utilizing the RAP protein, or its analogs, fragments or derivatives thereof, of the invention is to use them in methods of affinity chromatography to isolate and identify other proteins or factors to which they are capable of binding, e.g., other proteins or factors involved in the intracellular signaling process. In this application, the RAP protein, its analogs, fragments or derivatives thereof, of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the RAP protein, or its analogs, fragments or derivatives thereof of the invention, can be eluted, isolated and characterized.

(v) As noted above, the RAP protein, or its analogs, fragments or derivatives thereof, of the invention may also be used as immunogens (antigens) to produce specific antibodies thereto. These antibodies may also be used for the purposes of purification of the RAP protein (e.g., RAP or any of its isoforms) either from cell extracts or from transformed cell lines producing RAP protein, or its analogs or fragments. Further, these antibodies may be used for diagnostic purposes for identifying disorders related to abnormal functioning of the RIP-mediated FAS-R ligand or TNF system, or independent RIP activities, e.g., overactive or underactive FAS-R ligand- or TNF-induced cellular effects mediated by RIP or RIP's own specific cellular effects. Thus, should such disorders be related to a malfunctioning intracellular signaling system involving the RIP protein, or various other, above noted RIP-binding proteins or RAP protein itself, such antibodies would serve as an important diagnostic tool.

It should also be noted that the isolation, identification and characterization of the RAP protein of the invention may be performed using any of the well known standard screening procedures. For example, one of these screening procedures, the yeast two-hybrid procedure as is set forth herein below, was used to identify the RIP protein (see Stanger et al., 1995) and subsequently the various RAP proteins of the invention (besides various other new proteins of the above and below noted co-owned co-pending patent applications). Likewise as noted above and below, other procedures may be employed such as affinity chromatography, DNA hybridization procedures, etc. as are well known in the art, to isolate, identify and characterize the RAP protein of the invention or to isolate, identify and characterize additional proteins, factors, receptors, etc. which are capable of binding to the RAP proteins of the invention.

As set forth hereinabove, the RAP protein may be used to generate antibodies specific to RAP proteins, e.g., RAP and its isoforms. These antibodies or fragments thereof may be used as set forth hereinbelow in detail, it being understood that in these applications the antibodies or fragments thereof are those specific for RAP proteins.

Based on the findings in accordance with the present invention that RAP binds specifically to RIP and as such is a mediator/modulator of RIP and can thus mediate/modulate RIP's activity in inflammation, cell death or cell survival pathways in ways that RIP functions independently or in conjunction with other proteins (e.g. FAS-R, p55-R, MORT-1, MACH, Mch4, G1 and TRADD in cell death pathways, or with Traf2 in cell survival pathways) it is of importance to design drugs which may enhance or inhibit the RAP-RIP interaction, as desired and depending on which of these pathways are enhanced/inhibited by the RAP-RIP interaction. There are many diseases in which such drugs can be of great help. Amongst others, acute hepatitis in which the acute damage to the liver seems to reflect FAS-R ligand-mediated death of the liver cells; autoimmune-induced cell death such as the death of the β Langerhans cells of the pancreas, that results in diabetes; the death of cells in graft rejection (e.g., kidney, heart and liver); the death of oligo-dendrocytes in the brain in multiple sclerosis; and AIDS-inhibited T cell suicide which causes proliferation of the AIDS virus and hence the AIDS disease.

It is possible that RAP or one or more of its possible isoforms may serve as "natural" inhibitors of RIP in one or more of the above pathways and these may thus be employed as the above noted specific inhibitors of RIP. Likewise, other substances such as peptides, organic compounds, antibodies, etc. may also be screened to obtain specific drugs which are capable of inhibiting the RAP-RIP interaction.

A non-limiting example of how peptide inhibitors of the RAP-RIP interaction would be designed and screened is based on previous studies on peptide inhibitors of ICE or ICE-like proteases, the substrate specificity of ICE and strategies for epitope analysis using peptide synthesis. The minimum requirement for efficient cleavage of peptide by ICE was found to involve four amino acids to the left of the cleavage site with a strong preference for aspartic acid in the $P_1$ position and with methylamine being sufficient to the right of the $P_1$ position (Sleath et al., 1990; Howard et al., 1991; Thornberry et al., 1992). Furthermore, the fluorogenic substrate peptide (a tetrapeptide), acetyl-Asp-Glu-Val-Asp-a-(4-methyl-coumaryl-7-amide) abbreviated Ac-DEVD-AMC, corresponds to a sequence in poly (ADP-ribose) polymerase (PARP) found to be cleaved in cells shortly after FAS-R stimulation, as well as other apoptopic processes (Kaufmann, 1989; Kaufmann et al., 1993; Lazebnik et al., 1994), and is cleaved effectively by CPP32 (a member of the CED3/ICE protease family) and MACH proteases (and likewise also possibly by G1 proteases—see for example co-owned co-pending IL 120367).

As Asp in the $P_1$ position of the substrate appears to be important, tetrapeptides having Asp as the fourth amino acid residue and various combinations of amino acids in the first three residue positions can be rapidly screened for binding to the active site of the proteases using, for example, the method developed by Geysen (Geysen, 1985; Geysen et al., 1987) where a large number of peptides on solid supports were screened for specific interactions with antibodies. The binding of MACH proteases to specific peptides can be detected by a variety of well known detection methods within the skill of those in the art, such as radiolabeling of the G1 proteases, etc. This method of Geysen's was shown to be capable of testing at least 4000 peptides each working day.

In a similar way the exact binding region or region of homology which determines the interaction between RAP and RIP can be elucidated and then peptides may be screened which can serve to block this interaction, e.g. peptides synthesized having a sequence similar to that of the binding region or complementary thereto which can compete with natural RAP for binding to RIP.

Drug or peptide inhibitors, which are capable of inhibiting inflammation or the cell death activity of RAP by inhibiting the RAP-RIP interaction can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g. myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), $\alpha$-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of the RAP-RIP interaction according to the present invention is meant to include peptidomimetic drugs or inhibitors, which can also be rapidly screened for binding to RAP/RIP protease to design perhaps more stable inhibitors.

It will also be appreciated that the same means for facilitating or enhancing the transport of peptide inhibitors across cell membranes as discussed above are also applicable to the RAP or its isoforms themselves as well as other peptides and proteins which exert their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, *Nature,* 256:495–497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992–1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314: 268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066–1074 (1986); Robinson et al., International Patent Application No. W08702671 (published May 7, 1987); Liu et al., *Proc. Natl. Acad. Sci USA* 84:3439–3443 (1987); Sun et al., *Proc. Natl. Acad. Sci USA* 84:214–218 (1987); Better et al., *Science* 240:1041–1043 (1988); and Harlow and Lane, ANTIBODIES:A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the RAP proteins, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above RAP protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med* . 24:316–325 (1983)).

It will be appreciated that Fab and F(ab')2 and other fragments of the antibodies useful in the present invention may be used for the detection and quantitation of the RAP protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the RAP protein in a sample or to detect presence of cells which express the RAP protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the RAP protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the RAP protein, but also its distribution on the examined tissue. Using the present invention, those of ordinary skill will readily perceive that any of wide variety of histological methods (such as staining procedures) can be modified in order to achieve such in situ detection.

Such assays for the RAP protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the RAP protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholin-esterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}E$, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The RAP proteins of the invention may be produced by any standard recombinant DNA procedure (see for example, Sambrook, et al., 1989 and Ansabel et al., 1987–1995, supra) in which suitable eukaryotic or prokaryotic host cells well known in the art are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins, produced by the transformed hosts, are the derivatives produced by standard modification of the proteins or their analogs or fragments.

The present invention also relates to pharmaceutical compositions comprising recombinant animal virus vectors encoding the RAP proteins, which vector also encodes a virus surface protein capable of binding specific target cell (e.g., cancer cells) surface proteins to direct the insertion of the RAP protein sequences into the cells. Further pharmaceutical compositions of the invention comprises as the active ingredient (a) an oligonucleotide sequence encoding an anti-sense sequence of the RAP protein sequence, or (b) drugs that block the RAP-RIP interaction.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as well known to those of skill in the art.

The RAP protein and its isoforms or isotypes are suspected to be expressed in different tissues at markedly different levels and apparently also with different patterns of isotypes in an analogous fashion to the expression of various other proteins involved in the intracellular signaling pathways as indicated in the above listed co-owned co-pending patent applications. These differences may possibly contribute to the tissue-specific features of response to the Fas/APO1-ligand and TNF. As in the case of other CED3/ICE homologs (Wang et al., 1994; Alnemri et al., 1995), the present inventors have previously shown (in the above mentioned patent applications) that MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. A similar inhibitory effect of at least some G1 isoforms is also suspected (G1 being a recently isolated new Mch4- and possibly MACH-binding protein, and also MORT-1-binding protein that has MORT MODULES and a protease domain—see co-owned co-pending IL 120367). The wide heterogeneity of MACH isoforms, and likewise the suspected, analogous heterogeneity of G1 isoforms, which greatly exceeds that observed for any of the other proteases of the CED3/ICE family, should allow a particularly fine tuning of the function of the active MACH isoforms, and by analogy also the active G1 isoforms. Hence, as noted above, the RAP proteins or possible isoforms may have varying effects in different tissues as regards their interaction with RIP and their influence thereby on the balance between activation of cell death or cell survival pathways, as described above.

It is also possible that some of the possible RAP isoforms serve other functions. For example, RAP or some RAP isoforms may also act as docking sites for molecules that are involved in other, non-cytotoxic effects of Fas/APO1 and TNF receptors via interaction with RIP or even independently of RIP.

Due to the unique ability of Fas/APO1 and TNF receptors to cause inflammation, cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. Other aspects of the invention will be apparent from the following examples.

The invention will now be described in more detail in the following non-limiting examples and the accompanying drawings.

It should also be noted that the procedures of: i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, (see also Boldin et al., 1995b) 2, 3 (see also Boldin et al., 1996) and 4, below, with respect to MORT-1 and a MORT-1 binding protein, (e.g. MACH), as well as the newly isolated protein G1 (see IL 120367) are equally applicable (with some modifications) for the corresponding isolation, cloning and characterization of RAP and its possible isoforms of the present invention. These procedures are thus to be construed as the full disclosure of the same procedures used for the isolation, cloning and characterization of RAP in accordance with the present invention, as detailed e.g. in the same or equivalent form in the co-owned co-pending Israel Application Nos. 114,615, 114,986, 115,319, 116588, 117,932, and 120367 as well as the corresponding PCT application No. PCT/US96/10521. Further, as regards the NIK protein and its role in activating NF-κB and hence cell survival and the role played by Traf2 in this cell survival pathway, for example the interaction between Traf2 and RIP and other proteins, these have been detailed by the present inventors in co-pending co-owned IL 117800, IL 119133 and Malinin et al., 1997.

EXAMPLE

Cloning and Isolation of the RAP Protein which Binds to the RIP Protein (i) Two-hybrid Screen Sequencing and Preliminary Analysis Using the two-hybrid screen (see e.g. Fields and Song, 1989, WO/96/18641) with RIP devoid of its death domain as the bait in a B-cell library, a clone of about 1.9 Kb size was isolated and sequenced.

Primers from the 5' end of this sequence were designed and prepared. Employing PCR several cDNA libraries were screened. From both, a colon cDNA library and a heart cDNA library a clone of about 0.3 kB was obtained and ligated to the about 1.9 kB clone obtained from the B-cell library.

The new clone of about 2.2 kB, designated RAP-1 and deposited with Collection Nationale De Cultures De Microorganismes (CNCM), Institut Pasteur, 28, rue du Dr. Roux, 75724 Paris Cedex 15, France, on Jul. 26, 2001, under accession number I-2706, was sequenced (SEQ ID NO:1) and its deduced amino acid sequence determined (SEQ ID NO:2). Although the laboratory of the present inventors believes that the obtained sequences are correct, the possibility that there is an anomaly that leads to an error in sequencing cannot be ruled out completely. Nevertheless, the nucleotide and amino acid sequences are inherent in the deposit clone.

Analysis of the sequence shows that the RAP protein apparently does not have a 'death domain', it does not have a MORT MODULE, it does not have a protease domain like those of the ICE family, it does not have a kinase domain, nor does it have TRAF domains (see above noted co-pending, co-owned patent applications and the various references, especially Malinin et al., 1997 with respect to all the various domains present in the intracellular signaling pathways). Binding studies revealed that RAP essentially only binds to RIP, RAP being unable to bind to TRADD, MORT-1, p55-R, p75-R and MACH.

Therefore, it appears that RAP is a specific RIP-binding protein that interacts/binds to RIP in a very specific way, possibly via a binding domain region which is not present in other intracellular signaling proteins isolated to date. As RAP appears to be a specific modulator/mediator of RIP intracellular activity having an important role in RIP's modulation/mediation of the inflammation and the cell death/cell survival pathways.

Briefly, a clone of the RAP protein was obtained following two-hybrid screening of a human peripheral blood lymphocyte two-hybrid cDNA library using a fragment of RIP protein devoid of RIP's "death domain" region as 'bait'.

The RIP sequence was available from previous publications (e.g. Stanger et al., 1995) and as present in the GenBank database under accession No. U 25994 which is the human RIP sequence (also present was the mouse RIP sequence under accession No. U 25995). Using this sequence information appropriate PCR-primers were designed by OLIGO4™ software and the DNA fragment corresponding to the coding part of RIP, but without its C-terminal 'death domain' region was obtained by PCR using as template cDNA from the total RNA Human Fibroblast Cell library (using standard procedures). This coding part of RIP, devoid of RIP's 'death domain' region was then cloned into the pGBT-9 vector (Clontech) and used as a bait, as noted above, in the two-hybrid screening procedure. In this two-hybrid screen a number of clones were obtained all coding for proteins which are RIP-binding protein that interact with RIP at a region in RIP outside of the 'death domain' (C-terminus region of RIP), this not being present in the RIP 'bait'. After further proceedings as described above, the cDNA clone, the sequence of which is shown in FIG. 1 (SEQ ID NO:1), was obtained.

Analysis of the above sequences of the RAP clone and sequences in the 'dbest' database, Human Genome Database level 1 and GenBank database revealed that the RAP sequence is a unique (novel) sequence as no known sequence showed any significant homology to this RAP sequence.

Binding assay tests were performed to determine whether RAP can bind to any of the other known intracellular signaling proteins. In these tests the proteins TRADD, MORT-1, p55-R, p75-R, MACH were tested for their ability to bind to RAP. However, it was found that RAP was incapable of binding to any of these proteins. RAP also did not bind to any of the irrelevant control proteins, e.g. lamin, cyclin D.

All of the above results therefore indicate that the new RAP protein possibly interacts with RIP in a very specific manner and as such it represents a specific modulator/mediator of RIP. The exact site of interaction between RAP and RIP is yet to be determined but it seems that this site is one specific to RIP and RAP and not shared by other proteins known to interact with RIP, e.g. MORT-1, TRADD, FAS-R and possibly also Traf2 (see Malinin et al., 1997). It also arises that (from sequence analysis and comparison with sequences in various databases as noted above) that RAP does not have a 'death domain', a MORT MODULE, a protease domain (e.g. ICE/CED3 motif), a kinase domain/motif nor TRAF domains. In line with this, preliminary biological activity analysis also revealed that RAP apparently has the following characteristics:

(i) RAP is not toxic to cells on its own when overexpressed;

(ii) RAP does not protect cells from TNF killing and thus is apparently not an inhibitor of TNF-induced cell cytotoxicity;

(iii) RAP does not induce NF-κB on its own:

(iv) RAP does block NF-κB activation by TRADD, RIP and p55 TNF-R;

(v) RAP was also found to block JNK (Jun kinase) induction caused by RIP.

In view of the aforementioned RAP therefore appears to be a highly specific RIP-binding protein and hence RIP modulator/mediator, that is likely to be involved in the RIP-mediated intracellular signaling pathways.

In light of the above it appears that RAP is involved in modulation/mediation of RIP's activities intracellularly, these being its involvement in the inflammation and cell death pathway (independently via its 'death domain' or via interaction with other proteins such as MORT-1, TRADD, p55-R, FAS-R and associated proteases such as MACH, Mch4, G1 and the like) and RIP's involvement in the cell survival pathway (NF-κB activation, possibly via interaction with Traf2). The possible ways in which RAP may modulate/mediate RIP's activity are detailed hereinabove, for example the RAP-RIP interaction may lead to enhancement of either the cell death or cell survival pathways, or it may lead to the inhibition of either the cell death or cell survival pathways, this enhancement or inhibition possibly being dependent on the relative activities of other members of these two opposing intracellular pathways. RAP may also act as a docking protein to provide for an aggregation of a number of RIP molecules and other RIP- or RAP-binding proteins, which aggregate may then function either in the direction of cell death or cell survival (or even both) depending on the relative activities/amounts of the other members of these pathways in the cell.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Alnemri, E. S. et al. (1995) J. Biol. Chem. 270:4312–4317.
Barinaga, M. (1993) Science 262:1512–1514.
Beg, A. A. and Baltimore, D. Science 274:782–784.
Beidler, J. et al., (1995) J. Biol. Chem. 270:16526–16528.
Berger, J. et al., (1988) Gene 66:1–10.
Beutler, B. and Cerami, C. (1987) NEJM: 316:379–385.
Bigda, J. et al. (1994) J. Exp. Med. 180:445–460.
Boldin, M. P. et al. (1995a) J. Biol. Chem. 270:337–341.
Boldin, M. P. et al. (1995b) J. Biol. Chem. 270:7795–7798.
Boldin, M. P. et al. (1996) Cell 85:803–815.
Brakebusch, C. et al. (1992) EMBO J., 11:943–950.
Brockhaus, M. et al. (1990) Proc. Natl. Acad. Sci. USA, 87:3127–3131.
Cantor, G. H. et al. (1993) Proc. Natl. Acad. Sci. USA 90:10932–6.
Cerreti, D. P. et al. (1992) Science 256:97–100.
Chen, C. J. et al. (1992) Ann. N.Y. Acad. Sci. 660:271–3.
Chinnaiyan et al. (1995) Cell 81:505–512.
Chinnaiyan et al. (1996) J. Biol. Chem. 271:4961–4965.
Cifone, M. G. et al. (1995) EMBO J. 14:5859–5868.
Clement, M. V. et al. (1994) J. Exp. Med. 180:557–567.
Crisell, P. et al., (1993) Nucleic Acids Res. (England) 21 (22):5251–5.
Current Protocols in Molecular Biology (Ausubel, F. M., Brent, R., Kingston, R. E., Moore, D. D., Seidman, J. G., Smith, J. A., Struhl, K., Albright, L. M., Coen, D. M. & Varki, A., eds.), (1994) pp. 8.1.1–8.1.6 and 16.7–16.7.8, Greene Publishing Associates, Inc. and Wiley & Sons, Inc., New York.
Dirks, W., et al., (1993) Gene 128:247–249.
Durfee, T. et al. (1993) Genes Dev. 7:555–569.
Eischen, C. M. et al. (1994) J. Immunol. 153:1947–1954.
Ellis, H. M. et al. (1986) Cell 44:817–829.
Enari, M. et al. (1995) Nature 375:78–81.
Engelmann, H. et al. (1990) J. Biol. Chem., 265:1531–1536.
Faucheu, C. et al. (1995) EMBO J. 14:1914–1922.
Fernandes-Alnemri, T. et al. (1994) J. Biol. Chem. 269: 30761–30764.
Fernandes-Alnemri, T. et al. (1995) Cancer Res. 55:2737–2742.
Fernandes-Alnemri, T. et al. (1996) Proc. Natl. Acad. Sci. USA 93:7464–7469.
Field, J. et al. (1988) Mol. Cell Biol. 8:2159–2165.
Fields, S. and Song, O. (1989) Nature, 340:245–246.
Frangioni, J. V. and Neel, B. G. (1993) Anal. Biochem. 210:179–187.
Geysen, H. M. (1985) Immunol. Today 6:364–369.
Geysen, H. M. et al. (1987) J. Immunol. Meth. 102:259–274.
Gossen, M. and Boujard, H. (1992) Proc. Natl. Acad. Sci. USA, 89:5547–5551.
Grell, M. et al. (1994) Eur. J. Immunol. 24:2563–2566.
Heller, R. A. et al. (1990) Proc. Natl. Acad. Sci. USA, 87:6151–6155.
Henkart, P. A. (1996) Immunity 4:195–201.
Hohmann, H.-P. et al. (1989) J. Biol. Chem., 264:14927–14934.
Howard, A. D. et al. (1991) J. Immunol. 147:2964–2969.
Hsu, H. et al. (1995) Cell 81:495–504.
Hsu, H. et al. (1996) Cell 84:299–308.
Itoh, N. et al. (1991) Cell 66:233.
Itoh, N. and Nagata, S. (1993) J. Biol. Chem. 268:10932–7.
Joseph, S. and Burke, J. M. (1993) J. Biol. Chem. 268: 24515–8.
Kamens, J. et al. (1995) J. Biol. Chem. 270:15250–15256.
Kaufmann, S. H. (1989) Cancer Res. 49:5870–5878.
Kaufmann, S. H. (1993) Cancer Res. 53:3976–3985.
Kischkel, F. C. et al. (1995) EMBO J. 14:5579–5588.
Koizumi, M. et al. (1993) Biol. Pharm. Bull (Japan) 16 (9):879–83.
Kumar, S. et al. (1994) Genes Dev. 8:1613–1626.
Kumar, S. (1995) Trends Biochem Sci. 20:198–202.
Lazebnik, Y. A. et al. (1994) Nature 371:346–347.
Leithauser, F. et al. (1993) Lab Invest. 69:415–429.
Loetscher, H. et al. (1990) Cell, 61:351–359.
Los, M. et al. (1995) Nature 375:81–83.
Malinin, N. L. et al. (1997) Nature 385:540–544.
Martin, S. J. et al. (1995) J. Biol. Chem. 270:6425–6428.
Mashima, T. et al. (1995) Biochem. Biophys. Res. Commun. 209:907–915.
Miller, B. E. et al. (1995) J. Immunol. 154:1331–1338.
Milligan, C. E. et al. (1995) Neuron 15:385–393.
Miura, M. et al. (1995) Proc. Natl. Acad. Sci. USA 92:8318–8322.
Munday, N. A. et al. (1995) J. Biol. Chem. 270:15870–15876.
Muranishi, S. et al. (1991) Pharm. Research 8:649.
Nagata, S. and Golstein, P. (1995) Science 267, 1449–1456.
Nicholson, D. W. et al. (1995) Nature 376:37–43.
Nophar, Y. et al. (1990) EMBO J., 9:3269–3278.
Piquet, P. F. et al. (1987) J. Exp. Med., 166:1280–89.
Ray et al. (1992) Cell 69:597–604.
Ruggiero, V. et al. (1987) Cell Immunol. 107:317–325.
Sambrook et al. (1989) Molecular Cloning: A Laboratory Manual, Cold Spring Harbor Laboratory Press, Cold Spring Harbor, N.Y.
Schall, T. J. et al. (1990) Cell, 61:361–370.
Schlegel, et al. (1996) J. Biol. Chem. 271:1841–1844.
Schulze-Osthoff, K. et al. (1994) EMBO J. 13:4587–4596.
Shimayama, T. et al., (1993) Nucleic Acids Symp. Ser. 29:177–8
Shore, S. K. et al. (1993) Oncogene 8:3183–8.
Sleath, P. R. et al. (1990) J. Biol. Chem. 265:14526–14528.
Smith, C. A. et al. (1990) Science, 248:1019–1023.
Song, H. Y. et al. (1994) J. Biol. Chem. 269:22492–22495.
Srinivasula, S. M. et al. (1996) Proc. Natl. Acad. Sci. USA 93:14486–14491.
Stanger, B. Z. et al. (1995) Cell 81:513–523.
Tartaglia, L. A. et al. (1993) Cell, 74:845–853.
Tewari, M. et al. (1995) J. Biol. Chem. 270:3255–3260.
Tewari, M. et al. (1995a) J. Biol. Chem. 270:18738–18741.
Tewari, M. et al. (1995b) Cell 81:1–20.
Thornberry, N. A. et al. (1992) Nature 356:768–774.
Thornberry, N. A. et al. (1994) Biochemistry 33:3934–3940.
Tracey, J. T. et al. (1987) Nature, 330:662–664.
Van Antwerp, D. J. et al. (1996) Science 274:787–789.
Vandenabeele, P. et al. (1995) Trends Cell Biol. 5:392–400.
Vassalli, P. (1992) Ann. Rev. Immunol. 10:411–452.
Wallach, D. (1984) J. Immunol. 132:2464–9.
Wallach, D. (1986) In: Interferon 7 (Ion Gresser, ed.), pp. 83–122, Academic Press, London.
Wallach, D. et al. (1994) Cytokine 6:556.
Wang, L. et al. (1994) Cell 78:739–750.
Wang, C.-Y et al., (1996) Science 274:784–787.
Watanabe-Fukunaga, R. et al. (1992) Nature, 356:314–317.
Watanabe, F. R. et al. (1992) J. Immunol. 148:1274–1279.
Weitzen, M. et al. (1980) J. Immunol. 125:719–724.
Wilks, A. F. et al. (1989) Proc. Natl. Acad. Sci. USA, 86: 1603–1607.
Wong et al. (1994) J. Immunol. 152:1751–1755.
Xue, D. et al. (1995) Nature 377:248–251.
Yonehara, S. et al. (1989) J. Exp. Med. 169:1747–1756.
Yuan, J. et al. (1993) Cell 75:641–652.
Zaccharia, S. et al. (1991) Eur. J. Pharmacol. 203:353–357.
Zhao, J. J. and Pick, L. (1993) Nature (England) 365: 448–51.

What is claimed is:

1. An isolated polypeptide which is capable of binding to receptor interacting protein (RIP), which polypeptide comprises:
    (a) a RIP-associated protein (RAP) encoded by a DNA sequence in a clone deposited with Collection Nationale de Cultures de Microorganismes under accession number I-2706;
    (b) an analog of (a) having no more than five changes in the amino acid sequence of (a), each said change being a substitution, deletion or insertion of an amino acid, which analog binds to RIP; or
    (c) a derivative of (a) or (b) by modification of a functional group which occurs as a side chain or an N- or C-terminal group of one or more amino acid to another of the twenty commnly-occurring natural amino acids, which derivative binds to RIP.

2. The polypeptide according to claim 1, comprising a protein whose amino acid sequence is that of SEQ ID NO:2.

3. A composition comprising the polypeptide according to claim 1, and a pharmaceutically acceptable carrier.

4. An isolated polypeptide which is capable of binding to receptor interacting protein (RIP), which polypeptide consists of:

(a) a RIP-associate protein (RAP) encoded by a DNA sequence in a clone deposited with Collection Nationale de Cultures de Microorganismes under accession number I-2706;

(b) a fragment of (a), which fragment binds to RIP; or (c) a derivative of (a) or (b) by modification of a functional group which occurs as a side chain or an N- or C-terminal group of one or more amino acid residues thereof without changing one amino acid to another of the twenty commonly-occurring natural amino acids, which derivative binds to RIP.

5. The polypeptide in accordance with claim 1, wherein said analog of (c) has no more than three said changes in the amino acid sequence of (a).

6. The polypeptide in accordance with claim 1, wherein said analog of (c) has no more than one said change in the amino acid sequence of (a).

7. An isolated polypeptide which is capable of binding to receptor interacting protein (RIP), which polypeptide comprises:

(a) a RIP-associated protein (RAP) encoded by a DNA sequence in a clone deposited with Collection Nationale de Cultures de Microorganismes under accession number I-2706;

(b) an analog of (a) having no more than ten changes in the amino acid sequence of (a), each said change being a substitution of an amino acid, which analog binds to RIP; or (c) a derivative of (a) or (b) by modification of a functional group which occurs as a side chain or an N- or C-terminal group of one or more amino acid residues thereof without changing one amino acid to another of the twenty commonly-occurring natural amino acids, which derivative binds to RIP.

8. An isolated polypeptide which is capable of binding to receptor interacting protein (RIP), which polypeptide consists of:

(a) a RIP-associate protein (PAP) encoded by a DNA sequence in a clone deposited with Collection Nationale de Cultures de Microorganismes under accession number I-2706;

(b) a fragment of (a), which fragment binds to RIP;

(c) an analog of (a) having no more than five changes in the amino acid sequence of (a), each said change being a substitution of an amino acid, which analog binds to RIP; or
(d) a derivative of (a), (b) or (c) by modification of a functional group which occurs as a side chain or an N- or C-terminal group of one or more amino acid residues thereof without changing one amino acid to another of the twenty commonly-occurring natural amino acids, which derivative binds to RIP.

* * * * *

SEQUENCE LISTING

<160> NUMBER OF SEQ ID NOS: 2

<210> SEQ ID NO 1
<211> LENGTH: 2119
<212> TYPE: DNA
<213> ORGANISM: Homo sapiens
<220> FEATURE:
<221> NAME/KEY: CDS
<222> LOCATION: (217)..(1782)

<400> SEQUENCE: 1

```
tagggagacc caagcttctc gacggccatt accaatcgcg aaaccggcag ggcggccact      60 gtggcgggc tctttccccg tttcgcctca gctacccctc agctccggta gtcgccagtc     120
cggggtcgtc gccgtttggg gcgggagctg ctcggccccg ccgccgtccc cgtcgccgct     180
tccgggtcca ggcccctcgg gccgcctgcc gccgtc atg agg ctg cgg gtg cgg      234
                                       Met Arg Leu Arg Val Arg
                                         1               5 ctt ctg aag cgg acc tgg ccg ctg gag gtg ccc gag acg gag ccg acg      282
Leu Leu Lys Arg Thr Trp Pro Leu Glu Val Pro Glu Thr Glu Pro Thr
             10                  15                  20 ctg ggg cat ttg cgc tcg cac ctg agg ctg tcc ctg ctg tgc acc tgg      330
Leu Gly His Leu Arg Ser His Leu Arg Leu Ser Leu Leu Cys Thr Trp
         25                  30                  35 ggg tac agt tct aat acc cga ttt aca att aca ttg aac tac aag gat      378
Gly Tyr Ser Ser Asn Thr Arg Phe Thr Ile Thr Leu Asn Tyr Lys Asp
 40                  45                  50 ccc ctc act gga gat gaa gag acc ttg gct tca tat ggg att gtt tct      426
Pro Leu Thr Gly Asp Glu Glu Thr Leu Ala Ser Tyr Gly Ile Val Ser
55                  60                  65                  70 ggg gac ttg ata tgt ttg att ctt caa gat gac att cca gcg cct aat      474
Gly Asp Leu Ile Cys Leu Ile Leu Gln Asp Asp Ile Pro Ala Pro Asn
                 75                  80                  85 ata cct tca tcc aca gat tca gag cat tct tca ctc cag aat aat gag      522
Ile Pro Ser Ser Thr Asp Ser Glu His Ser Ser Leu Gln Asn Asn Glu
             90                  95                 100 caa ccc tct ttg gcc acc agc tcc aat cag act agc atg cag gat gaa      570
Gln Pro Ser Leu Ala Thr Ser Ser Asn Gln Thr Ser Met Gln Asp Glu
        105                 110                 115 caa cca agt gat tca ttc caa gga cag gca gcc cag tct ggt gtt tgg      618
Gln Pro Ser Asp Ser Phe Gln Gly Gln Ala Ala Gln Ser Gly Val Trp
    120                 125                 130 aat gac gac agt atg tta ggg cct agt caa aat ttt gaa gct gag tca      666
Asn Asp Asp Ser Met Leu Gly Pro Ser Gln Asn Phe Glu Ala Glu Ser
135                 140                 145                 150 att caa gat aat gcg cat atg gca gag ggc aca ggt ttc tat ccc tca      714
Ile Gln Asp Asn Ala His Met Ala Glu Gly Thr Gly Phe Tyr Pro Ser
                155                 160                 165 gaa ccc atg ctc tgt agt gaa tcg gtg gaa ggg caa gtg cca cat tca      762
Glu Pro Met Leu Cys Ser Glu Ser Val Glu Gly Gln Val Pro His Ser
            170                 175                 180 tta gag acc ttg tat caa tca gct gac tgt tct gat gcc aat gat gcc      810
Leu Glu Thr Leu Tyr Gln Ser Ala Asp Cys Ser Asp Ala Asn Asp Ala
        185                 190                 195 ttg ata gtg ttg ata cat ctt ctc atg ttg gag tca ggt tac ata cct      858
Leu Ile Val Leu Ile His Leu Leu Met Leu Glu Ser Gly Tyr Ile Pro
    200                 205                 210 cag ggc acc gaa gcc aaa gca ctg tcc atg ccg gag aag tgg aag ttg      906
Gln Gly Thr Glu Ala Lys Ala Leu Ser Met Pro Glu Lys Trp Lys Leu
```

```
                    215                 220                 225                 230
agc ggg gtg tat aag ctg cag tac atg cat cct ctc tgc gag ggc agc        954
Ser Gly Val Tyr Lys Leu Gln Tyr Met His Pro Leu Cys Glu Gly Ser
                    235                 240                 245 tcc gct act ctc acc tgt gtg cct ttg gga aac ctg att gtt gta aat       1002
Ser Ala Thr Leu Thr Cys Val Pro Leu Gly Asn Leu Ile Val Val Asn
            250                 255                 260 gct aca cta aaa atc aac aat gag att aga agt gtg aaa aga ttg cag       1050
Ala Thr Leu Lys Ile Asn Asn Glu Ile Arg Ser Val Lys Arg Leu Gln
        265                 270                 275 ctg cta cca gaa tct ttt att tgc aaa gag aaa cta ggg gaa aat gta       1098
Leu Leu Pro Glu Ser Phe Ile Cys Lys Glu Lys Leu Gly Glu Asn Val
    280                 285                 290 gcc aac ata tac aaa gat ctt cag aaa ctc tct cgc ctc ttt aaa gac       1146
Ala Asn Ile Tyr Lys Asp Leu Gln Lys Leu Ser Arg Leu Phe Lys Asp
295                 300                 305                 310 cag ctg gtg tat cct ctt ctg gct ttt acc cga caa gca ctg aac cta       1194
Gln Leu Val Tyr Pro Leu Leu Ala Phe Thr Arg Gln Ala Leu Asn Leu
                315                 320                 325 cca gat gta ttt ggg ttg gtc gtc ctc cca ttg gaa ctg aaa cta cgg       1242
Pro Asp Val Phe Gly Leu Val Val Leu Pro Leu Glu Leu Lys Leu Arg
            330                 335                 340 atc ttc cga ctt ctg gat gtt cgt tcc gtc ttg tct ttg tct gcg gtt       1290
Ile Phe Arg Leu Leu Asp Val Arg Ser Val Leu Ser Leu Ser Ala Val
        345                 350                 355 tgt cgt gac ctc ttt act gct tca aat gac cca ctc ctg tgg agg ttt       1338
Cys Arg Asp Leu Phe Thr Ala Ser Asn Asp Pro Leu Leu Trp Arg Phe
    360                 365                 370 tta tat ctg cgt gat ttt cga gac aat act gtc aga gtt caa gac aca       1386
Leu Tyr Leu Arg Asp Phe Arg Asp Asn Thr Val Arg Val Gln Asp Thr
375                 380                 385                 390 gat tgg aaa gaa ctg tac agg aag agg cac ata caa aga aaa gaa tcc       1434
Asp Trp Lys Glu Leu Tyr Arg Lys Arg His Ile Gln Arg Lys Glu Ser
                395                 400                 405 ccg aaa ggg cgg ttt gtg atg ctc ctg cca tcg tca act cac acc att       1482
Pro Lys Gly Arg Phe Val Met Leu Leu Pro Ser Ser Thr His Thr Ile
            410                 415                 420 cca ttc tat ccc aac ccc ttg cac cct agg cca ttt cct agc tcc cgc       1530
Pro Phe Tyr Pro Asn Pro Leu His Pro Arg Pro Phe Pro Ser Ser Arg
        425                 430                 435 ctt cct cca gga att atc ggg ggt gaa tat gac caa aga cca aca ctt       1578
Leu Pro Pro Gly Ile Ile Gly Gly Glu Tyr Asp Gln Arg Pro Thr Leu
    440                 445                 450 ccc tat gtt gga gac cca atc agt tca ctc att cct ggt cct ggg gag       1626
Pro Tyr Val Gly Asp Pro Ile Ser Ser Leu Ile Pro Gly Pro Gly Glu
455                 460                 465                 470 acg ccc agc cag ttt cct cca ctg aga cca cgc ttt gat cca gtt ggc       1674
Thr Pro Ser Gln Phe Pro Pro Leu Arg Pro Arg Phe Asp Pro Val Gly
                475                 480                 485 cca ctt cca gga cct aac ccc atc ttg cca ggg cga ggc ggc ccc aat       1722
Pro Leu Pro Gly Pro Asn Pro Ile Leu Pro Gly Arg Gly Gly Pro Asn
            490                 495                 500 gac aga ttt ccc ttt aga ccc agc agg ggt cgg cca act gat ggc cgg       1770
Asp Arg Phe Pro Phe Arg Pro Ser Arg Gly Arg Pro Thr Asp Gly Arg
        505                 510                 515 ctg tca ttc atg tgattgattt gtaatttcat ttctggagct ccatttgttt          1822
Leu Ser Phe Met
        520 ttgtttctaa actacagatg tcaactcctt ggggtgctga tctcgagtgt tattttctga    1882
```

-continued

```
ttgtggtgtt gagagttgca ctcccagaaa cctttttaaga gatacattta tagccctagg    1942
ggtggtatga cccaaaggtt cctctgtgac aaggttggcc ttgggaatag ttggctgcca    2002
atctccctgc tcttggttct cctctagatt gaagtttgtt ttctgatgct gttcttacca    2062
gattaaaaaa aagtgtaaat taaaaaaaaa aaaaaaaaa aaaaaaaaaa aaaaaa         2119
```

<210> SEQ ID NO 2
<211> LENGTH: 522
<212> TYPE: PRT
<213> ORGANISM: Homo sapiens

<400> SEQUENCE: 2

```
Met Arg Leu Arg Val Arg Leu Leu Lys Arg Thr Trp Pro Leu Glu Val
1               5                   10                  15

Pro Glu Thr Glu Pro Thr Leu Gly His Leu Arg Ser His Leu Arg Leu
            20                  25                  30

Ser Leu Leu Cys Thr Trp Gly Tyr Ser Ser Asn Thr Arg Phe Thr Ile
        35                  40                  45

Thr Leu Asn Tyr Lys Asp Pro Leu Thr Gly Asp Glu Glu Thr Leu Ala
    50                  55                  60

Ser Tyr Gly Ile Val Ser Gly Asp Leu Ile Cys Leu Ile Leu Gln Asp
65                  70                  75                  80

Asp Ile Pro Ala Pro Asn Ile Pro Ser Ser Thr Asp Ser Glu His Ser
                85                  90                  95

Ser Leu Gln Asn Asn Glu Gln Pro Ser Leu Ala Thr Ser Ser Asn Gln
            100                 105                 110

Thr Ser Met Gln Asp Glu Gln Pro Ser Asp Ser Phe Gln Gly Gln Ala
        115                 120                 125

Ala Gln Ser Gly Val Trp Asn Asp Asp Ser Met Leu Gly Pro Ser Gln
    130                 135                 140

Asn Phe Glu Ala Glu Ser Ile Gln Asp Asn Ala His Met Ala Glu Gly
145                 150                 155                 160

Thr Gly Phe Tyr Pro Ser Glu Pro Met Leu Cys Ser Glu Ser Val Glu
                165                 170                 175

Gly Gln Val Pro His Ser Leu Glu Thr Leu Tyr Gln Ser Ala Asp Cys
            180                 185                 190

Ser Asp Ala Asn Asp Ala Leu Ile Val Leu Ile His Leu Leu Met Leu
        195                 200                 205

Glu Ser Gly Tyr Ile Pro Gln Gly Thr Glu Ala Lys Ala Leu Ser Met
    210                 215                 220

Pro Glu Lys Trp Lys Leu Ser Gly Val Tyr Lys Leu Gln Tyr Met His
225                 230                 235                 240

Pro Leu Cys Glu Gly Ser Ser Ala Thr Leu Thr Cys Val Pro Leu Gly
                245                 250                 255

Asn Leu Ile Val Val Asn Ala Thr Leu Lys Ile Asn Asn Glu Ile Arg
            260                 265                 270

Ser Val Lys Arg Leu Gln Leu Leu Pro Glu Ser Phe Ile Cys Lys Glu
        275                 280                 285

Lys Leu Gly Glu Asn Val Ala Asn Ile Tyr Lys Asp Leu Gln Lys Leu
    290                 295                 300

Ser Arg Leu Phe Lys Asp Gln Leu Val Tyr Pro Leu Leu Ala Phe Thr
305                 310                 315                 320

Arg Gln Ala Leu Asn Leu Pro Asp Val Phe Gly Leu Val Val Leu Pro
                325                 330                 335
```

-continued

```
Leu Glu Leu Lys Leu Arg Ile Phe Arg Leu Leu Asp Val Arg Ser Val
            340             345             350

Leu Ser Leu Ser Ala Val Cys Arg Asp Leu Phe Thr Ala Ser Asn Asp
        355             360             365

Pro Leu Leu Trp Arg Phe Leu Tyr Leu Arg Asp Phe Arg Asp Asn Thr
    370             375             380

Val Arg Val Gln Asp Thr Asp Trp Lys Glu Leu Tyr Arg Lys Arg His
385             390             395             400

Ile Gln Arg Lys Glu Ser Pro Lys Gly Arg Phe Val Met Leu Leu Pro
            405             410             415

Ser Ser Thr His Thr Ile Pro Phe Tyr Pro Asn Pro Leu His Pro Arg
            420             425             430

Pro Phe Pro Ser Ser Arg Leu Pro Pro Gly Ile Ile Gly Gly Glu Tyr
        435             440             445

Asp Gln Arg Pro Thr Leu Pro Tyr Val Gly Asp Pro Ile Ser Ser Leu
    450             455             460

Ile Pro Gly Pro Gly Glu Thr Pro Ser Gln Phe Pro Pro Leu Arg Pro
465             470             475             480

Arg Phe Asp Pro Val Gly Pro Leu Pro Gly Pro Asn Pro Ile Leu Pro
            485             490             495

Gly Arg Gly Gly Pro Asn Asp Arg Phe Pro Phe Arg Pro Ser Arg Gly
            500             505             510

Arg Pro Thr Asp Gly Arg Leu Ser Phe Met
            515             520
```